United States Patent [19]

Lin

[11] Patent Number: 4,604,210

[45] Date of Patent: Aug. 5, 1986

[54] METHOD FOR REMOVING CYCLIC PHOSPHORUS CONTAMINANTS FROM ORGANIC SUBSTRATES

[75] Inventor: Chung-Yuan Lin, Northford, Conn.

[73] Assignee: The Dow Chemical Company, Midland, Mich.

[21] Appl. No.: 727,178

[22] Filed: Apr. 25, 1985

[51] Int. Cl.$^4$ ............................................... B01D 15/04
[52] U.S. Cl. ..................................... 210/690; 210/906
[58] Field of Search ................ 210/660, 690, 692, 906

[56] References Cited

U.S. PATENT DOCUMENTS

| | | | |
|---|---|---|---|
| 4,014,935 | 3/1977 | Ibbotson | 260/566 R |
| 4,156,065 | 5/1979 | Onder et al. | 528/51 |
| 4,202,964 | 5/1980 | Pruckmayr | 528/482 |
| 4,272,382 | 6/1981 | Ogata et al. | 210/690 |

*Primary Examiner*—Ivars Cintins
*Attorney, Agent, or Firm*—James S. Rose

[57] ABSTRACT

A method is disclosed for removing certain contaminant phospholene and pholpholane oxides or sulfides from organic fluid or fluid mixtures wherein the fluid or fluid mixture is contacted with a cation exchange resin insoluble in the mixture at a temperature of from about 20° C. to about 100° C.

11 Claims, No Drawings

METHOD FOR REMOVING CYCLIC PHOSPHORUS CONTAMINANTS FROM ORGANIC SUBSTRATES

FIELD OF THE INVENTION

This invention relates to the separation of cyclic phosphorus compounds from organic substrates and is more particularly concerned with the removal of certain phospholene or phospholane contaminants from a fluid or fluid mixture.

DESCRIPTION OF THE PRIOR ART

The use of cyclic phosphorus compounds as catalysts in a number of industrial organic chemical procedures has increased dramatically of late. This is particularly true in the area relating to the partial carbodiimidization of organic polyisocyanates for the formation of stabilized polyisocyanates. U. S. Patent 4,014,935 is a typical reference in this regard which discloses the use of certain cyclic phospholene and phospholane catalysts.

Similar phosphorus compounds are employed as catalysts in the preparation of a wide variety of polyamide, polyimide, and polyamideimide polymers from the reaction of organic isocyanates with carboxylic acids and/or anhydrides; for example, see U.S. Pat. No. 4,156,065.

Generally speaking, the removal of these phosphorus containing catalysts from their reaction environments or resulting products is difficult. In some cases the residual catalyst is even left in the product to avoid this difficulty. U.S. No. 4,014,935 cited supra discloses two methods for the removal of catalysts from the products: one by adsorption on clays or activated carbon; the other by the addition of various chemical agents. The reference states a preference for the latter chemical treatment wherein all of the chemical contaminants are actually left in the product. Furthermore, the use of activated carbons and various clays suffer from the disadvantage that their adsorbent properties vary tremendously from batch to batch so as to be essentially non-reproducible.

An area of major concern is the contamination of large volumes of reaction solvents by these cyclic phosphorus compounds and the problems such contamination create. This type of problem is encountered in the preparation of the polymers described in U.S. No. 4,156,065 above. While the polymer product is obtained relatively free of catalyst contamination by virtue of its precipitation from the solvent, the solvent itself is contaminated and its recovery in purified form presents difficulties.

I have now discovered that certain acidic exchange resins will efficiently remove certain cyclic phosphorus contaminants from organic fluids or fluid mixtures. Surprisingly, it was found that only the acidic resins would effectively remove the contaminants as opposed to the basic resins. Closely related acidic resins have been reported in U.S. Pat. No. 4,202,964 as removing oligomeric cyclic ethers from linear tetrahydrofuran-/alkylene oxide polymerizates. However, to the best of my knowledge, the present method represents the first time such cyclic phosphorus contaminants have been effectively removed from organic substrates using acidic exchange resins.

SUMMARY OF THE INVENTION

This invention comprises a method for removing cyclic phosphorus contaminants selected from those having the formulae (I) and (II) (see FORMULA CHART)

wherein a, b, c, and d in each instance are independently selected from the group consisting of hydrogen, halogen, lower-alkoxy, phenoxy, lower-hydrocarbyl, and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; R is selected from the group consisting of lower-hydrocarbyl and halo-substituted lower-hydrocarbyl, and Z is selected from the class consisting of oxygen and sulfur from a fluid or fluid mixture, said method comprising contacting the fluid or fluid mixture with a cation exchange resin insoluble therein at a temperature of from about 20° C. to about 100° C. and thereafter separating said exchange resin from said fluid or fluid mixture.

The term "halogen" is used throughout this specification and claims in its generally accepted sense as embracing chlorine, bromine, iodine, and fluorine.

The term "lower-alkoxy" as used throughout the specification and claims means alkoxy from 1 to 6 carbon atoms, inclusive, such as methoxy, ethoxy, propoxy, butoxy, pentyloxy, hexyloxy and isomeric forms thereof. The term "lower-hydrocarbyl" means the monovalent radical obtained by removing one hydrogen atom from a parent hydrocarbon having from 1 to 6 carbon atoms, inclusive. Illustrative of such hydrocarbyl groups are alkyl such as methyl, ethyl, propyl, butyl, pentyl, hexyl and isomeric forms thereof; alkenyl such as vinyl, allyl, butenyl, pentenyl, hexenyl, and isomeric forms thereof; cycloalkyl such as cyclobutyl, cyclopentyl and cyclohexyl; and phenyl.

The term "halo-substituted lower-hydrocarbyl" means lower-hydrocarbyl as above defined wherein one or more of the hydrogen atoms in said hydrocarbyl has been replaced by halogen. Illustrative of halo-substituted lower-hydrocarbyl are chloromethyl, trichloromethyl, trifluoromethyl, 2-chloroethyl, 2,3-dichlorobutyl, 2-chlorobutenyl, 2-bromohexyl, 4-chlorophenyl, 3-fluorophenyl, 2-chloropropenyl, and the like.

The term "contaminant" means the cyclic phosphorus compound is present at a concentration of less than about 1 percent by weight based on the total weight of the contaminated fluid or fluid mixture.

The term "fluid or fluid mixture" means any organic compound or mixtures thereof in fluid form and is inclusive of liquids, solids dissolved in liquids, and mixtures thereof.

DETAILED DESCRIPTION OF THE INVENTION

The present method provides a novel means for selectively separating or removing cyclic phosphorus contaminants, defined above and discussed in detail below, from any organic substrate provided the substrate is a fluid or fluid mixture. The fluid substrate is simply brought into intimate contact with a cation exchange resin either in a batchwise or continuous procedure using known methods. Unless the substrate material itself should be protected from atmospheric moisture, oxygen, light, or the like, no particular precautions are required during the time the resin and substrate are in contact.

Accordingly, in a batchwise procedure any type of vessel or autoclave provided with an efficient means for agitation can be used to intimately mix the resin and substrate. In an optional and preferable embodiment, the mixing vessel is equipped with means for heating and also a reflux system in order to contain any low boiling liquids which might reach their reflux temperatures.

Alternatively, in a continuous process any suitable chamber or column having a packed section containing the resin is employed. In this case, circulation means are provided to recirculate the fluid substrate through the section of packed resin until the contaminant has been removed. Additionally, the column can be equipped with heating means and a heat exchanger tube for the recirculation of any condensed vapors.

The batchwise method is preferred primarily because of its simplicity both in operation and equipment requirements.

Advantageously, the contacting step is carried out at a temperature of from about 20° C. to about 100° C. Preferably, the temperature is within the range of from about 25° C. to about 60° C. In some cases the use of elevated temperatures is employed as much for lowering the viscosity of the fluid or fluid mixture as it is to aid the adsorption process itself.

The contact time to remove the majority of the contaminant will vary widely depending on such factors as concentration of the contaminant, amount of resin employed and its acidity content, temperature, viscosity of the fluid or fluid mixture, and the like. Generally speaking, the level of contaminant will be reduced by at least 90 percent by weight of its original level which level, as noted above, is less than about 1 percent by weight to begin with.

Accordingly, the fluid or fluid mixture is contacted with the resin for a time sufficient to reduce the contaminant level by at least 90 percent, and, preferably, at least 95 percent by weight of its original level.

The progress of contaminant removal can be monitored by conventional analytical procedures and methods with gas phase chromatography (GC) being particularly useful. Aliquot samples are removed and filtered to separate the resin and analysis carried out on the filtrate using known GC procedures.

Upon completion of the process the solid resin is separated from the substrate using any known method for separating solids from liquids such as simple filtration, either under atmospheric or reduced pressure, centrifugation, decantation, and the like. In the event a continuous process is employed, then the separating step is automatically carried out when the fluid leaves the column for the last time.

Simple filtration methods are preferred and in some cases when the resin is used in finely divided form, a filter aid such as Filtercel or Celite is advantageously employed.

As defined above, the cyclic phosphorus contaminants removed by the present method are those having the formulae (I) and (II). These compounds belong to a class of phospholenes and phospholanes which are particularly useful as carbodiimide forming catalysts and catalysts for polyamide and polyimide polymer formation as discussed above. For a detailed exemplification of these compounds see the U.S. Pat. Nos. 4,014,935 and 4,156,065 cited supra whose disclosures relative thereto are incorporated herein by reference.

The preferred method in accordance with the present invention comprises the removal of phospholene oxide compounds of formula (Ia) (see FORMULA CHART) wherein a, b, c, d, Y and R have the same definition set forth above for (I). In a most preferred method a, b, c, and d in each instance are independently selected from hydrogen and lower-alkyl, and R is selected from lower-alkyl and phenyl.

The fluid or fluid mixture from which the contaminants are removed, as defined above, represent a broad group of organic liquids, organic solids dissolved in organic solutions, mixtures of these and the like. It will be readily understood by those skilled in the art that if it be a solid material which is to be purified, then it is simply dissolved in a convenient solvent prior to being contacted with the resin. Alternatively, the solid may already be in solution as a crude reaction mixture.

In respect of the organic fluids or fluid mixtures which can be purified in accordance with the present invention the following are meant to be illustrative only and not limiting thereof: aromatic solvents such as benzene, toluene, xylene, chloro- and dichlorobenzene, nitrobenzene, and the like; aliphatic ketones such as acetone, methylethyl ketone, diethyl ketone, and the like; esters such as ethyl acetate, butyl acetate, ethyl propionate, butyl propionate, and the like; chlorinated aliphatic solvents such as methylene dichloride, chloroform, carbon tetrachloride, tetrachloroethane, and the like; dipolar aprotic solvents such as acetonitrile, formamide; dimethylformamide; N,N-dimethylacetamide, tetramethylene sulfone, dimethyl sulfone, dimethyl sulfoxide, tetramethylurea, hexamethylphosphoramide, and the like; glyme (dimethylether of ethylene glycol), diglyme (dimethylether of diethylene glycol), triglyme (dimethylether of triethylene glycol) and the like; any of the solid organic solvents such as decalin or tetralin can be either dissolved in another solvent to form a fluid component or else heated to their fluid state prior to treatment; liquid isocyanates and mixtures thereof such as those disclosed in U.S. No. 4,014,935 cited supra; the viscous to solid oligomeric aromatic carbodiimide mixtures as produced typically in U.S. No. 3,502,722; the solid polycarbodiimide polymers as disclosed typically in U.S. No. 2,941,966; the mixed aliphatic/aromatic polycarbodiimides as produced according to U.S. No. 4,487,964; and the like.

The present method is particularly adaptable to the purification of organic solvents and oligomeric aromatic carbodiimide mixtures.

The cation exchange resins used are commercially available and can be any of the acidic cationic ion exchange resins bearing —SO$_3$H or —COOH groups provided the resin is insoluble in the fluid or fluid mixture. Generally speaking, those resins bearing the —SO$_3$H groups are strongly acidic and are preferred over the weaker acidic resins bearing the —COOH groups.

The amount of exchange resin employed is advantageously from about 1 to about 300 parts by weight per 1 part by weight of said contaminant.

Preferably, the resin is used within the range of about 10 to about 200 parts per 1 part of contaminant.

The nature of the backbone of the resin is unimportant. The most common commercially available resins have backbones which are cross-linked copolymers of styrene and divinyl benzene but resins having other backbones can be used. Generally speaking, the resins fall into the two broad categories of either the gel type or macroreticular type and both are useful in the present method. The macroreticular type of resins due to their high pore diameter and long life are preferred.

Typical of a preferred macroreticular resin for use in the present method is Amberlyst ®-15 sold by Rohm & Haas Company. This is a strongly acidic —SO$_3$H type resin having a surface area of about 45 square meters per gram, an initial porosity of 0.3–0.35 milliliter of pore per milliliter of bead and an initial average pore diameter of 200–600 Angstrom units.

Illustrative of a strongly acidic ion exchange resin having a different backbone than the more common polystyrene/divinyl benzene is one based on a copolymer of tetrafluoroethylene and exemplified in Nafion ® H supplied by E. I. du Pont de Nemours as disclosed in U.S. Pat. No. 3,692,569.

Generally speaking, resins can be used directly as obtained from the supplier without any pretreatment. Although in some instances it is expedient to provide an acidwash prior to their use; for a detailed description of such an acid pretreatment step see U.S. Pat. No. 4,202,964 whose disclosure relative thereto is incorporated herein by reference. The resins have a long active life and are easily regenerated using well-known methods for reactivation of ion exchange resins including the acid pretreatment above.

The resins can be employed in their bead or finely divided form as supplied and in some cases it is advantageous to use them in powdered form in order to provide greater surface area of resin to the contaminant.

Surprisingly, the basic anion exchange resins are not useful in the present method because they cannot remove the cyclic phosphorus compounds to any substantial degree. This is even more surprising considering the high polarity of the contaminants arising from the phosphorus to oxygen or phosphorus to sulfur bond. It would be expected a priori that both the acidic and basic resins would be equally useful or equally not useful.

The utility of the present process has been amply discussed above. Suffice it to say that the method can be used to purify organic compounds including monomeric materials, oligomers, such as the oligomeric aromatic polycarbodiimides described above, polymers including polycarbodiimides discussed above, and the like. A particularly useful application of the present method is in the purification and recovery of organic solvents which have been exposed to the phosphorus containing contaminants.

The following examples describe the manner and process of making and using the invention and set forth the best mode contemplated by the inventor of carrying out the invention but are not to be construed as limiting.

EXAMPLE 1

The following experiment describes two separate runs 1 and 2 in which a major proportion of a phospholene oxide contaminant was removed from each of two tetramethylene sulfone (TMS) solutions in accordance with the present invention. The TMS stock solution used in each case contained an isomer mixture consisting of 1,3-dimethyl-2-phospholene-1-oxide and 1,3-dimethyl-3-phospholene-1-oxide (hereinafter DMPO) in the approximate proportions of 75/25, respectively. The TMS was analyzed by gas phase chromatography (GC) using a Hewlett Packard 5830A GC and column packing OV 101 (15 meters length) fused silica glass capillary column (purchased from Quadrex Corp.); operated at 160° C.-200° C. column temperature.

The concentration of the DMPO was observed to be $5 \times 10^{-4}$ g. per gram of TMS solution.

In run 1, 20 g. of the tetramethylene sulfone solution and 2 grams of powdered Amberlyst ®-15 which is a macroreticular strongly acidic cation exchange resin having SO$_3$H groups (supplied by Mallinckrodt, Inc.) were stirred together for 2 hours at about 60° C. in a reaction flask equipped with stirrer, thermometer and reflux condenser. At the end of the two hour period the resin was removed by filtration with the aid of a filter aid material (Filtercel). The filtrate was then analyzed by the GC method described above for the DMPO content.

Run 2 was carried out identically to run 1 except that 2 g. of Nafion ® H was employed. This resin is also a strongly acidic cation exchange resin having SO$_3$H groups and is supplied by E. I. du Pont. The filtrate was also analyzed by GC analysis as above.

The filtrate from run 1 was also subjected to an MDI test which was found to be an efficient and rather sensitive test for determining the tolerated level of residual DMPO in the treated TMS solution. The test was carried out by first purging the solution with nitrogen for about 3 hours at about 130° C. in order to remove traces of moisture. Then a 0.5 g. aliquot of the treated TMS was added to 1 g. of 4,4'-methylenebis(phenyl isocyanate) [MDI] in a small glass jar which was heated at 100° C. to form a homogeneous solution. The liquefied sample was then capped and stored in an oven at 60° C. for observation with time. If the DMPO level remaining in the TMS is above a certain level, then its effect in catalyzing the formation of carbodiimide in the MDI can be observed as the liquefied sample gels. At high levels of DMPO, the sample can be observed to actually foam and gel.

The observed data set forth in Table I shows that the control sample receiving no treatment had a DMPO content of $5 \times 10^{-4}$ g/g. of TMS solution and when subjected to the MDI test it caused the MDI to gel in only 2 hours. Run 1 was observed to have a DMPO concentration of $2.4 \times 10^{-5}$ g/g. TMS which amounted to a 95.2% removal of contaminant. A sample from run 1 when subjected to the MDI test was completely fluid or liquid for at least 35 days.

Run 2 in accordance with the invention had a DMPO content of $1.3 \times 10^{-5}$ or 97.4% removal. It was not subjected to the MDI test.

TABLE I

|  | Control | Run 1 Amberlyst ®-15 | Run 2 Nafion ® H |
|---|---|---|---|
| Conc. of DMPO: (g/g. of TMS) | $5 \times 10^{-4}$ | $2.4 \times 10^{-5}$ | $1.29 \times 10^{-5}$ |
| % DMPO removal |  | 95.2% | 97.4% |
| MDI Test | gel in 2 hrs. | liquid for at least 35 days | — |

EXAMPLE 2

A stock contaminated chlorobenzene solution was prepared in which the concentration of the DMPO contaminant, described in Example 1, in the chlorobenzene solvent was 0.1 g. per 20 g. of solution.

Five separate 20 g. samples of this stock solution were treated with five different powdered exchange resins using the same procedure described in Example 1 above except that only 1 gram of each resin was employed in each case. Runs 3 to 6 inclusive are in accordance with the present invention, whereas run 7 is not because a basic exchange resin was employed. Duplicate runs were carried out using the resin in bead form as obtained from the supplier except for run 6.

All of the filtered solutions were analyzed using the GC method described above but instead of determining the absolute concentration of DMPO, the percentage remaining was determined by area comparison of the new to the original GC peak.

The MDI test, where employed, differed from that described above in Example 1 only in that the proportions of test solution and MDI were 0.5 g. and 8 g., respectively.

The results observed are set forth in Table II with the data observed for those runs using the resin in bead form appearing in parenthesis. The highly acidic resins in runs 3, 4 and 6 show the more efficient DMPO removal, whereas run 5 which is a weaker acid resin was not as efficient at least in powdered form. Comparison run 7 which empolyed a weakly basic resin left a high proportion of DMPO in the chlorobenzene. The MDI test indicated that at a residual 1.5% of the original DMPO level the solution was quite stable in regard to the polymerization of the MDI. Contrastingly, at a 7.1% level as in run 5 the MDI test sample gelled overnight.

g. of the residue with 8 g. MDI. The sample foamed and gelled overnite in the oven at 50° C.

The carbodiimide residue was redissolved in 50 ml. of methylene dichloride and stirred under reflux (about 40° C.) with an additional 0.6 g. of Amberlyst ®-15 (powdered) for 2 hours. A filter aid was required when removing the powdered resin from the solution. The solution was treated as above and this time when the residue was subjected to the MDI test the sample remained a liquid for a period longer than 12 days.

A separate 0.5 g. sample of the oligomeric product was dissolved in 8 g. of MDI, stored overnite at the 50° C. temperature and then analyzed for isocyanate content using standard analytical methods. The calculated isocyanate equivalent weight taking into consideration the addition of 0.5 g. of oligomeric product (assumed to be inert to NCO) was 132.8; observed was 136. Therefore, the concentration of DMPO in the carbodiimide product was very low.

FORMULA CHART

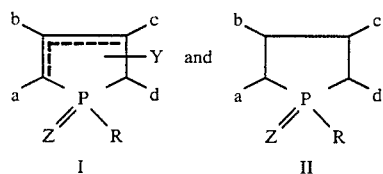

TABLE II*

|  | Run 3 Amberlyst ®-15 | Run 4 Amberlyst ®[1] XN-1010 | Run 5 Amberlite ®[2] IRC-50 | Run 6 Nafion ® H | Run 7 Comparison[3] Amberlyst ® A-21 |
| --- | --- | --- | --- | --- | --- |
| % DMPO remaining | 1.5% (4.5%) | 1.5% (16.5%) | 7.1% (11.4%) | 4% | 65% (59.5%) |
| MDI Test | remains liquid at least 20 days (gels in 5 days) | — | gel overnight (gel overnight) | — | gel overnight (gel overnight) |

*Percentage figures and test comments in parenthesis refer to the results observed when the exchange resin was employed in bead rather than powdered form.
Footnotes to TABLE II
[1]Amberlyst ® XN-1010 is a strongly acidic cation exchange resin having SO3H groups and a very high surface area (540 sq. meters/gm.); supplied by Alfa Products.
[2]Amberlite ® IRC-50 is a weakly acid cation exchange resin having COOH groups and is supplied by Alfa Products.
[3]Amberlyst ® A-21 is a weakly basic anion exchange resin having —N(CH3)2 groups and is supplied by Alfa Products.

EXAMPLE 3

A 100 ml. reaction flask equipped with a stirrer, thermometer, reflux condenser, and nitrogen inlet tube was charged with 8.7 g. (0.024 mole) of 3,3',5,5'-tetraethyl-4,4'-methylenebis(phenyl isocyanate), 2.14 g. (0.012 mole) of 2,6-diethylphenyl isocyanate, 0.03 g. DMPO and 10 ml. of chlorobenzene.

During continual stirring under nitrogen the reaction solution was heated at 130° C. for about 18 hours. An infrared spectrum of an aliquot showed the absence of unreacted isocyanate and formation of carbodiimide linkages. Thus, there was obtained a solution of an oligomeric aromatic carbodiimide mixture.

A 40 ml. portion of methylene dichloride was added to the carbodiimide solution followed by 0.6 g. of Amberlyst ®-15 (16-50 mesh). The mixture was stirred under mild reflux (about 40° C.) for 2 hours. The mixture was filtered to remove the resin and all of the solvent was removed from the filtrate using a rotary evaporator under about 10 mm. of mercury pressure. The viscous brown liquid residue was subjected to the MDI test in accordance with Example 2 above by mixing 0.5

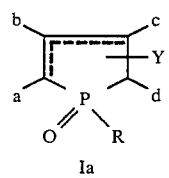

Ia

I claim:
1. A method for removing a cyclic phosphorus contaminant selected from those having the formulae:

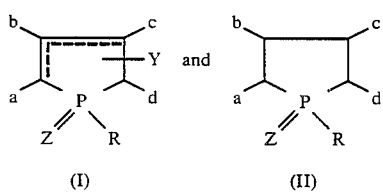

wherein
a, b, c, and d in each instance are independently selected from the group consisting of hydrogen, halogen, lower-alkoxy, phenoxy, lower-hydrocarbyl and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; R is selected from the group consisting of lower-hydrocarbyl and halo-substituted lower-hydrocarbyl, and Z is selected from the class consisting of oxygen and sulfur from a fluid or fluid mixture selected from the group consisting of an organic liquid, an organic solid dissolved in an organic liquid, an mixtures of any of the foregoing, said method comprising contacting the fluid or fluid mixture with a cation exchange resin insoluble therein at a temperature of from about 20° C. to about 100° C. and thereafter separating said exchange resin from said fluid or fluid mixture.

2. A method according to claim 1 wherein said contaminant is a phospholene oxide having the formula

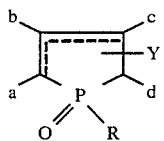

(Ia)

wherein a, b, c, and d in each instance are independently selected from the group consisting of hydrogen, halogen, lower-alkoxy, phenoxy, lower-hydrocarbyl, and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; and R is selected from the group consisting of lower-hydrocarbyl and halo-substituted lower-hydrocarbyl.

3. A method according to claim 2 wherein in said contaminant a, b, c, and d in each instance are independently selected from hydrogen and lower-alkyl, and R is selected from lower-alkyl and phenyl.

4. A method according to claim 2 comprising contacting the fluid or fluid mixture with from about 1 to about 300 parts by weight of a strongly acidic cation exchange resin per 1 part by weight of said contaminant at a temperature of from about 25° C. to about 60° C. and thereafter separating said exchange resin from said fluid or fluid mixture.

5. A method according to claim 4 wherein said contaminant is a mixture of 1,3-dimethyl-2-phospholene-1-oxide and 1,3-dimethyl-3-phospholene-1-oxide.

6. A method according to claim 5 wherein said fluid or fluid mixture is the organic solvent tetramethylene sulfone.

7. A method according to claim 5 wherein said fluid or fluid mixture is the organic solvent chlorobenzene.

8. A method according to claim 5 wherein said fluid or fluid mixture is a solution comprising an oligomeric aromatic carbodiimide mixture prepared from the reaction of 3,3',5,5'-tetraethyl-4,4'-methylenebis(phenyl isocyanate) and 2,6-diethylphenyl isocyanate in a 2:1 molar proportion respectively in chlorobenzene.

9. A method according to claim 1 wherein the amount of said exchange resin is from about 1 to about 300 parts by weight per 1 part by weight of said contaminant.

10. A method according to claim 1 wherein the temperature is from about 25° C. to about 60° C.

11. A method according to claim 1 wherein said exchange resin is a strongly acidic cation exchange resin.

* * * * *